US006506393B2

(12) United States Patent
Eibl et al.

(10) Patent No.: US 6,506,393 B2
(45) Date of Patent: *Jan. 14, 2003

(54) METHODS OF TREATING PROTOZOAL DISEASES

(75) Inventors: Hansjörg Eibl, Bovenden-Eddigehausen (DE); Clemens Unger, Göttingen (DE); Jürgen Engel, Alzenau (DE)

(73) Assignees: Zentaris AG, Frankfurt (DE); Max-Planck Gesellschaft zur Forderung der Wissenchaften e.V., Gottingen (DE)

( * ) Notice: Subject to any disclaimer, the term of this patent is extended or adjusted under 35 U.S.C. 154(b) by 24 days.

This patent is subject to a terminal disclaimer.

(21) Appl. No.: 09/799,505

(22) Filed: Mar. 7, 2001

(65) Prior Publication Data

US 2001/0008885 A1 Jul. 19, 2001

Related U.S. Application Data

(62) Division of application No. 09/359,405, filed on Jul. 23, 1999, now Pat. No. 6,254,879, which is a continuation-in-part of application No. 08/469,779, filed on Jun. 6, 1995, now Pat. No. 5,980,915, which is a continuation of application No. 08/238,343, filed on May 5, 1994, now abandoned, which is a continuation of application No. 07/948,052, filed on Sep. 21, 1992, now abandoned.

(30) Foreign Application Priority Data

Sep. 27, 1991 (DE) .......................... 41 32 344

(51) Int. Cl.$^7$ ............ A61K 6/00; A61K 9/00; A61N 25/00; A61F 13/00; A01N 59/26
(52) U.S. Cl. .............. 424/401; 424/405; 424/78.06; 424/601; 424/464; 424/499; 514/859; 514/928
(58) Field of Search .................... 424/401, 7, 8.06, 424/601; 514/859, 928

(56) References Cited

U.S. PATENT DOCUMENTS

| 4,837,023 A | 6/1989 | Eibl |
| 5,049,552 A | 9/1991 | Eibl |
| 5,087,721 A | 2/1992 | Counsell |
| 5,155,099 A | 10/1992 | Brachwitz et al. |
| 5,980,915 A | * 11/1999 | Eibl et al. |

FOREIGN PATENT DOCUMENTS

| EP | 0 108 565 | * 10/1983 |
| EP | 0 108 565 | 5/1984 |
| EP | 0 230 575 | 8/1997 |

OTHER PUBLICATIONS

S.L. Croft et al., Biochemical Pharmacology, vol. 36, No. 16, pp. 2633–2636; 1987, "The Activity of Alkylphosphocholine and Related Derivatives Against Leishmaniasis in Mice".*

S.L. Croft et al., Biochemical Pharmacology, vol. 36, No. 16, pp. 2633–2636; 1987 "The Activity of Alkyl Phosphorylcholines and Related Derivatives Against Leishmania".

Antimicrobial Agents and Chemotherapy, vol. 36, No. 8, pp. 1630–1634, Aug. 1992, "Hexadecylphosphocholine: Oral Treatment of Visceral Leishmaniasis in Mice".

British Medical Journal, Sep. 14, 1985, "Topical Treatment of Recurrent Cutaneous Leishmaniasis with Ointment Containing Paromomycin and Methylbenzethonium Chloride".

The American Journal of Topical Medicine and Hygiene, vol. 35, vol. 6, Nov. 1986, pp. 1110–1116, "Leishmania Major: Antileishmanial Activity of Methylbenzethonium Chloride".

ACTA Tropica (1997), pp. 145–154, "Efficacy of Anticancer Alkylphosphocholines in Trypanosoma Brucei Subspecies".

Croft et al., Chem Abstract, 107: 168296C (1987).

* cited by examiner

Primary Examiner—Thurman K. Page
Assistant Examiner—Isis Ghali
(74) Attorney, Agent, or Firm—Arent Fox Kintner Plotkin & Kahn

(57) ABSTRACT

The invention concerns a new pharmaceutical agent for oral or topical administration in the treatment of protozoal diseases, in particular of leishmaniasis, which contains as the active substance one or several compounds having the general formula I

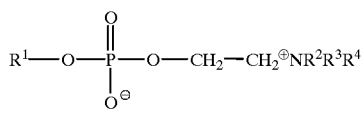

(I)

in which $R^1$ is a saturated or monounsaturated or polyunsaturated hydrocarbon residue with 12 to 20 C atoms and $R^2$, $R^3$ and $R^4$ denote independently of one another hydrogen, a $C_1$–$C_5$ alkyl group, a $C_3$–$C_6$ cycloalkyl group or a $C_1$–$C_5$ hydroxyalkyl group whereby two of the residues $R^2$, $R^3$ and $R^4$ can together form a $C_2$–$C_5$ alkylene group which, if desired, can be substituted with an —O—, —S— or $NR^5$ group, in which $R^5$ is hydrogen, a $C_1$–$C_5$ alkyl group, a $C_3$–$C_6$ cycloalkyl group or a $C_1$–$C_5$ hydroxyalkyl group as well as, if desired the usual pharmaceutical auxiliary, diluting, carrier or/and filling substances.

4 Claims, No Drawings

METHODS OF TREATING PROTOZOAL DISEASES

This is a divisional of application Ser. No. 09/359,405 filed Jul. 23, 1999, now U.S. Pat. No. 6,254,879, which is a Continuation-In-Part of application Ser. No. 08/469,779, filed Jun. 6, 1995, now U.S. Pat. No. 5,980,915 which is a continuation of application Ser No. 08/238,343, filed May 5, 1994, now abandoned which is continuation of application Ser. No. 07/948,052, filed Sep. 21, 1992 now abandoned. The disclosure of the prior application(s) is hereby incorporated by reference herein in its entirety.

DESCRIPTION

The present invention concerns a process for the production of a pharmaceutical agent for oral or topical administration in the treatment of protozoal diseases, in particular of leishmaniasis.

Leishmaniasis is a name for various tropical diseases which are caused by flagellates of the genus Leishmania and is transmitted by various blood-sucking insects. The manifestations of leishmaniasis may be visceral (kala-azar), mucocutaneous (american leishmaniasis) or cutaneous (Aleppo boil or diffuse cutaneous leishmaniasis). The incubation period is weeks or months. A very high mortality rate is observed in untreated cases, in particular with kala-azar and american leishmaniasis.

The therapeutic agents used today for the treatment of leishmaniasis are pentavalent antimony compounds (e.g. sodium stibogluconate) and aromatic diamidines. A disadvantage of these drugs is, however, that they cause severe side-effects such as nausea and vomitting due to their high toxicity. Moreover there are already Leishmania strains which are resistant to antimony.

Croft et al (Biochem. Pharmacol. 36 (1987), p. 2633–2636) describe experiments in which the effectiveness of alkyl phosphocholines against Leishmania donovani was investigated. The effect of alkyl phosphocholines was tested in comparison with the effect of the standard therapeutic preparation, sodium stibogluconate, (Pentostam) when administered subcutaneously. In this process it was found that alkyl phosphocholines, in particular $C_{22}$ alkyl phosphocholines are active against Leishmania. It was, however, also established that the alkyl phosphocholines, in particular hexadecyl-phosphocholine, were highly toxic for the experimental animals, in particular for macrophages in therapeutically effective doses so that they do not represent a real alternative when administered subcutaneously to the known therapy with sodium stibogluconate.

Thus the object of the present invention was to provide a pharmaceutical agent for protozoal diseases, in particular for leishmaniasis, in which the disadvantages of the state of the art, in particular with regard to the severe side-effects, are at least partially eliminated.

The object according to the present invention is achieved by a process for the production of a pharmaceutical agent for oral or topical administration in the treatment of protozoal diseases, in particular of leishmaniasis, which contains as the active substance one or several compounds having the general formula I

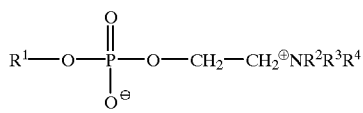

in which $R^1$ is a saturated or monounsaturated or polyunsaturated hydrocarbon residue with 12 to 20 C atoms and $R^2$, $R^3$ and $R^4$ denote independently of one another hydrogen, a $C_1$–$C_5$ alkyl group, a $C_3$–$C_6$ cycloalkyl group or a $C_1$–$C_5$ hydroxyalkyl group whereby two of the residues $R^2$, $R^3$ and $R^4$ can together form a $C_2$–$C_5$ alkylene group which, if desired, can be substituted with an —O—, —S— or $NR^5$ group, in which $R^5$ is hydrogen, a $C_1$–$C_5$ alkyl group, a $C_3$–$C_6$ cycloalkyl group or a $C_1$–$C_5$ hydroxyalkyl group as well as, if desired the usual pharmaceutical auxiliary, diluting, carrier or/and filling substances.

In the general formula I, $R^1$ can be branched or straight-chained. $R^1$ is preferably a straight-chained hydrocarbon residue with 16 to 20 C atoms, in particular a hexadecyl, octadecyl, oleyl, elaidyl, eicosyl or eicosenyl-cis-(ω-9) residue. $R^1$ is particularly preferably a hexadecyl or octadecyl residue.

Examples of suitable residues $R^2$, $R^3$ and $R^4$ in the formula I are for instance methyl, ethyl, propyl, butyl and pentyl residues, cyclopropyl, cyclobutyl, cyclopentyl and cyclohexyl residues, hydroxymethyl, hydroxyethyl and hydroxypropyl residues. Two of the residues $R^2$, $R^3$ and $R^4$ can for example form a pyrrolidine, a piperidine or a morpholine group. At least one of the residues $R^2$, $R^3$ and $R^4$ is preferably different from hydrogen, it is particularly preferred that all 3 residues are different from hydrogen.

Examples of preferred residues $R^2$, $R^3$ and $R^4$ are methyl, ethyl, hydroxyethyl and $C_3$–$C_6$ cycloalkyl residues. If one of $R^2$, $R^3$ and $R^4$ is a cycloalkyl residue, then the other two residues are preferably methyl residues. It is particularly preferred that the residues $R^2$, $R^3$ and $R^4$ are independently of each other methyl or ethyl residues. It is most preferred when $R^2$, $R^3$ and $R^4$ are methyl residues so that alkyl phosphocholines represent a particularly preferred class of compounds which is suitable for the production of an agent against protozoal diseases, in particular against leishmaniasis.

It was surprisingly found that compounds having the general formula I when administered orally or topically show no measurable side-effects and a very much higher activity than sodium stibogluconate. In any case the therapeutic agents according to the present invention constitute the first forms of oral therapy for leishmaniasis diseases, and they are considerably more effective than Pentostam, a standard therapeutic preparation used worldwide in the liver and in particular also in the spleen.

In a preferred embodiment of the present invention the oral or topical therapeutic preparation additionally contains one or several alkyl glycerols having the general formula II

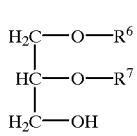

in which one of the residues $R^6$ and $R^7$ denotes an alkyl group with 2 to 12 C atoms and the other residue denotes a hydrogen atom. An alkyl glycerol mixture is preferably used which contains nonyl or octyl glycerol, hexyl or pentyl glycerol and propyl or ethyl glycerol as well as, if desired, water.

The pharmaceutical agent according to the present invention contains in one dosage unit preferably 5 to 2000 mg, particularly preferably 10 to 500 mg of one or several compounds having the general formula I. For topical administration the pharmaceutical agent according to the present invention preferably contains 5 to 200 mg of one or several compounds having the general formula I per ml of an alkyl glycerol having the formula II or of a corresponding alkyl glycerol mixture.

For oral administration the pharmaceutical agent according to the present invention is preferably formulated as a drinking solution with a daily dosage between 1 and 10 mg/kg of one or several compounds having the general formula I.

The production of an oral pharmaceutical agent according to the present invention can on the other hand also be carried out by mixing or homogenizing one or several compounds having the general formula I with the usual physiologically tolerated filling, carrier, dilution or/and auxiliary substances at temperatures between 20 and 120° C. and, if desired in order to prepare formulations which contain 10 to 800 mg of compounds having the general formula I in one dosage unit, the mixture thus obtained is poured into hollow cells of an appropriate size or filled into capsules of an appropriate size or granulated and then pressed into tablets, if desired, with addition of further common auxiliary substances. The active substance can for example be mixed with one or several of the following auxiliary substances: starch, cellulose, lactose, formalin-casein, modified starch, magnesium stearate, calcium hydrogenphosphate, highly-dispersed silicic acid, talcum and phenoxyethanol. The mixture obtained is granulated, if desired, with an aqueous solution containing for example gelatin, starch, polyvinyl pyrrolidone, vinylpyrrolidon-vinyl acetate copolymerisate or/and polyoxyethylene sobitanmonooleate, as constituent and the granulate is homogenized, if desired, with one or several of the aforementioned auxiliary substances. Subsequently this mixture can be pressed into tablets or filled into capsules whereby the tablets or capsules each contain 10 to 800 mg of active substance in one dosage unit.

In a particularly preferred embodiment the active substance is suspended with soybean lecithin as well as, if desired, 0.1 to 0.5 parts by weight phenoxyethanol (in relation to one part by weight of the active substance) at temperatures between 33 and 37° C. in melted resin fat and homogenized and subsequently the mixture is poured into hollow cells whereby one dosage unit contains 10 to 800 mg of the active substance.

Moreover the active substance can be homogenized at a temperature between 50 and 120° C., if desired in the presence of one or several emulsifiers or/and 0.1–0.5 parts by weight phenoxyethanol (in relation to 1 part by weight of the active substance) with at least one of the following substances: paraffin, vaseline, aliphatic alcohol with 12 to 25 C atoms, sorbitanmonopalmitate, aliphatic monocarboxylic acid with 15 to 20 C atoms, polyoxyethylenepolyol fatty acid ester. If desired, the mixture obtained can be emulsified with addition of a multivalent lower (preferably $C_2$–$C_3$) aliphatic alcohol (e.g. ethylene glycol, diethylene glycol, propylene glycol, dipropylene glycol and in particular glycerol).

On the other hand, if desired, the active substance can be dissolved at temperatures between 30 and 100° C. in the presence of 0.1–0.5 parts by weight phenoxyethanol (in relation to one part by weight of the active substance) as well as, if desired, in the presence of an emulsifier and if desired the solution thus obtained is filled up with sufficient water or vegetable oil so that the final solution contains 0.1 to 5 % by weight of the active substance.

The active substance can also be mixed together with an alkyl glycerol having the general formula II or with a mixture of such alkyl glycerols as well as, if desired, water in which 1 to 30 parts by weight alkyl glycerol having the general formula II or of a corresponding alkyl mixture and if desired 1 to 30 parts by weight water, each in relation to 1 part by weight active substance according to general formula I, are used.

The present invention also concerns the use of one or several compounds having the general formula I as the active substance for an oral or a topical agent for treating protozoal diseases, in particular leishmaniasis. In this connection the agent can additionally contain one or several alkyl glycerols having the general formula II, in particular for topical applications.

Finally the invention also concerns a process for the treatment of protozoal diseases, in particular of leishmaniasis, which is characterized in that a pharmaceutical agent produced according to the present invention is administered topically or orally.

The production of compounds having the general formula I is described in detail in the examples for hexadecylphosphocholine. Further methods for the production of compounds having the general formula I are described for example in DE-A 27 52 125, DE-A 36 41 379, DE-A 36 41 491, DE-A 40 13 632, DE-A 36 41 377, the literature cited in these or in earlier patent applications or patent specifications of the same applicant. Reference is expressly made to this literature for the present patent application.

The pharmaceutical agents according to the present invention are preferably used for the treatment of leishmaniasis. Other protozoal diseases which can be treated by the agent according to the present invention are for instance malaria, trypanosomiasis, toxoplasmosis, babesiosis, amoebic dysentery and lambliasis. The agents according to the present invention are in particular suitable for those diseases in which the pathogen is present in organs such as the liver, spleen or kidney.

It is intended to elucidate the invention further by the following examples.

EXAMPLE 1

Production of Hexadecylphosphocholine $H_2O$ a) Hexadecylphosphoethanolamine
(Phosphorylation, Ring Closure and Ring Opening)

Hexadecanol (1 mole, 243 g) and triethylamine (1.8 mole, 180 g) are dissolved in 1.5 l THF (tetrahydrofuran) and added dropwise to a solution of phosphoroxychloride (1.2 mole, 184 g) in 120 ml THF which was stirred vigorously in such a way that the temperature in the reaction vessel (three-neck, 5 l, with dropping funnel, thermometer and stirrer) does not exceed 10° C. In order to accelerate the process, the reaction vessel is cooled with an ice-salt mixture. The reaction is completed immediately after the dropwise addition (detected by TLC in ether: Rf values of 0.8 for the initial product, of 0.0 for the reaction product after hydrolysis with water).

The ice-bath is removed and a solution of ethanolamine (1.5 mole, 92 g) and triethylamine (1.8 mole, 180 g) in 1 l dioxan are added while stirring vigorously in such a way that the temperature in the reaction vessel increases to 65 to 70° C. Then the ring formation is completed (detected by TLC in ether: Rf values of 0.2). Precipitated triethylamine hydrochloride is removed by filtration while still warm and 1.5 l 2N formic acid is added to the filtrate at 40 to 50° C. After 15 minutes the ring opening is completed (detected by TLC in ether: Rf values 0.0; TLC in chloroform/methanol/acetic acid/water 100:60:20:5 by volume: Rf value 0.8). It is cooled to −20° C. and the precipitate which is mainly composed of pure hexadecylphosphoethanolamine is filtered off. If slight impurities are present a subsequent chromatographic purification is carried out.

| Microanalysis (MW 365.50): | | | | |
|---|---|---|---|---|
| calc. (%) | C 59.15 | H 11.03 | N 3.83 | P 8.48 |
| found (%) | 59.01 | 10.95 | 3.79 | 8.31 |

Methylation of Hexadecylphosphoethanolamine

The crystals obtained according to example 1 are taken up in 1.2 l 2-propanol and 0.4 l dichloromethane without further purification. Potassium carbonate (4 mole, 560 g) is added to the suspension of the crystals in 1 l water while stirring vigorously. Dimethyl sulfate (4 mole, 500 g) is added dropwise to the two-phase reaction mixture while stirring in such a way that the temperature does not exceed 40° C. The reaction is completed 60 minutes after the dropwise addition (detected by TLC in chloroform/methanol/25% ammonia 50:50:5 by volume: Rf value 0.3). After phase separation at 20° C., the upper phase contains the product. The solvent is removed in a rotary evaporator under a vacuum and the viscous residue is chromatographed on silica gel (Merck product No. 7733, silica gel 60, particle size 0.2 to 0.5 mm).
Chromatography Chloroform/methanol/25% ammonia (200/15/1 by volume) is added to 2 kg silica gel and filled into a chromatography column. The viscous oil is dissolved in 800 ml of the above solvent mixture and the crude product is applied to the column (insoluble components are previously removed by filtration). It is eluted with mobile solvents of increasing polarity until the impurities are washed out. The product is finally eluted with chloroform/methanol/25% ammonia (50/50/5 by volume). The combined eluates are rotary evaporated and the remaining water is removed with toluol. The residue is taken up in 600 ml dichloromethane and 4 l acetone is added. The crystals which separate out at −20° C. are washed with cold acetone, then with pentane and dried in a vacuum. The yield of pure hexadecylphospocholine is 250 g (ca. 70% in relation to hexadecylglycerol).

| Microanalysis (MW 407.58): | | | | |
|---|---|---|---|---|
| calc. (%): | C 59.27 | H 11.37 | N 3.29 | P 7.28 |
| found (%): | 58.98 | 11.31 | 3.21 | 7.11 |

Production of Pharmaceutical Formulations

Example for a Solution 25 g 1-n-propyloxy-2,3-propanediol, 12.5 g 1-n-hexyloxy-2,3-propanediol, 12.5 g 1-n-nonyloxy-2,3-propanediol, 44 g water and 1 g phenoxyethanol are mixed and 5 g hexadecylphosphocholine is dissolved in this mixture. The solution is freed of visible particles by filtration over suitable filters.

1 g solution contains 50 mg hexadecylphosphocholine.

Example for a an Ointment 5 g hexadecylphosphocholine is suspended in 35 g viscous paraffin, 30 g emulsified cetylstearyl alcohol and 30 g white vaseline are added and melted. This melt is first stirred until it has cooled down. A homogeneous distribution of active substance is achieved by processing the cooled melt by means of a suitable homogenizer (e.g. three-roll mill).

1 g of the hydrophilic ointment contains 50 mg hexadecylphosphocholine.

Example for an Emulsion 11.83 g 1-n-propyloxy-2,3-propanediol, 5.91 g 1-n-hexaloxy-2,3-propanediol, 5.91 g 1-n-nonyloxy-2,3-propanediol, 20.35 g water and 1.0 g phenoxyethanol are mixed and 5 g hexadecylphosphocholine is dissolved in this mixture. 30 g white vaseline, 15 g cetylalcohol and 5 g sorbitan monopalmitate are melted on a water-bath, heated to 70° C. and the solution of the active substance, which was also heated to 70° C., is emulsified in the fat phase with the aid of a high-speed dispersing apparatus. The cream is subsequently cooled down to 30° C. while stirring. 1 g water-in-oil cream contains 50 mg hexadecylphosphocholine.

Example for Capsules 1.25 kg hexadecylphospocholine is dissolved in 5 kg chloroform and 1.25 kg aerosil is suspended in this solution. The solvent is subsequently removed in a vacuum. The dry mass is passed through a 1 mm sieve and dried once again in a vacuum at 30° C. in order to remove any last remains of solvent. This granulate is filled in a known way to 500 mg into gelatin hard capsules with a size of 00 using a suitable capsule machine. One capsule contains 250 mg hexadecylphosphocholine.

Examples of Further Active Substances

EXAMPLE 2

Octadecylphosphocholine
$C_{23}H_{50}NO_4P$ MW 435.630

EXAMPLE 3

Oleylphosphocholine
$C_{23}H_{48}NO_4P$ MW 433.614

EXAMPLE 4

Elaidylphosphocholine
$C_{23}H_{48}NO_4P$ MW 433.614

EXAMPLE 5

Hexadecylphospho-(N.N-dimethyl-N-ethyl)ethanolamine MW 421.603

EXAMPLE 6

Octadecylphospho-(N.N-dimethyl-N-ethyl)ethanolamine MW 449.657

EXAMPLE 7

Oleylphospho-(N.N-dimethyl-N-ethyl)ethanolamine MW 447.641

EXAMPLE 8

Elaidylphospho-(N.N-dimethyl-N-ethyl)ethanolamine
MW 447.641

EXAMPLE 9

Hexadecylphospho-(N-cyclopropyl-N.N-dimethyl)-ethanolamine
$C_{23}H_{48}NO_4P$ MW 443.614

EXAMPLE 10

Hexadecylphospho-(N-cyclobutyl-N.N-dimethyl)-ethanolamine
$C_{24}H_{50}NO_4P$ MW 447.641

EXAMPLE 11

Hexadecylphospho-(N-cyclopentyl-N.N-dimethyl)-ethanolamine
$C_{25}H_{52}NO_4P$ MW 461.668

EXAMPLE 12

Hexadecylphospho-(N.N-dimethyl-N-hydroxyethyl)-ethanolamine
$C_{22}H_{48}NO_5P$ MW 437.602

EXAMPLE 13

Hexadecylphospho-(N-methyl)-pyrrolidino-ethyl ester
$C_{23}H_{48}NO_4P$ MW 433.614

EXAMPLE 14

Octadecylphospho-(N.N-diethyl-N-methyl)-ethanolamine
$C_{25}H_{54}NO_4P$ MW 463.684

EXAMPLE 15

Octadecylphospho-(N-cyclopropyl-N.N-dimethyl)-ethanolamine
$C_{25}H_{52}NO_4P$ MW 461.668

EXAMPLE 16

Octadecylphospho-(N-cyclobutyl-N.N-dimethyl)-ethanolamine
$C_{26}H_{54}NO_4P$ MW 475.695

EXAMPLE 17

Octadecylphospho-(N-cyclopentyl-N.N-dimethyl)-ethanolamine
$C_{27}H_{56}NO_4P$ MW 489.722

EXAMPLE 18

Octadecylphospho-(N.N-dimethyl-N-hydroxyethyl)-ethanolamine
$C_{24}H_{52}NO_4P$ MW 465.656

EXAMPLE 19

Octadecylphospho-(N-methyl)-pyrrolidino-ethyl ester
$C_{25}H_{52}NO_4P$ MW 461.668

EXAMPLE 20

Oleylphospho-(N.N-diethyl-N-methyl)-ethanolamine
$C_{25}H_{52}NO_4P$ MW 461.668

EXAMPLE 21

Oleylphospho-(N-cyclopropyl-N.N-dimethyl)-ethanolamine
$C_{25}H_{50}NO_4P$ MW 459.652

EXAMPLE 22

Oleylphospho-(N-cyclopentyl-N.N-dimethyl)-ethanolamine
$C_{27}H_{54}NO_4P$ MW 487.706

EXAMPLE 23

Oleylphospho-(n.N-dimethyl-N-hydroxyethyl)-ethanolamine
$C_{24}H_{50}NO_5P$ MW 463.640

EXAMPLE 24

Oleylphospho-(N-methyl)-pyrrolidino-ethyl ester
$C_{25}H_{50}NO_4P$ MW 459.652

EXAMPLE 25

Elaidylphospho-(N-cyclopropyl-N.N-dimethyl)-ethanolamine
$C_{25}H_{50}NO_4P$ MW 459.652

EXAMPLE 26

Elaidylphospho-(N.N-dimethyl-N-hydroxyethyl)-ethanolamine
$C_{24}H_{50}NO_5P$ MW 463.640

EXAMPLE 27

Elaidylphospho-(N-methyl)-pyrrolidino-ethyl ester
$C_{25}H_{50}NO_4P$ MW 459.652

EXAMPLE 28

Eicosylphosphocholine
$C_{25}H_{54}NO_4P$ MW 463.684

EXAMPLE 29

Eicosylphospho-(N-ethyl-N.N-dimethyl)-ethanolamine
$C_{26}H_{56}NO_4P$ MW 477.711

EXAMPLE 30

Eicosylphospho-(N.N-diethyl-N-methyl)-ethanolamine
$C_{27}H_{54}NO_4P$ MW 491.738

EXAMPLE 31

Eicosylphospho-(N-cyclopropyl-N.N-dimethyl)-ethanolamine
$C_{27}H_{56}NO_4P$ MW 489.722

EXAMPLE 32

Eicosylphospho-(N.N-dimethyl-N-hydroxyethyl)-ethanolamine
$C_{26}H_{56}NO_5P$ MW 493.710

EXAMPLE 33

Eicosylphospho-(N.N-dihydroxyethyl-N-methyl)-ethanolamine $C_{27}H_{58}NO_6P$ MW 523.736

EXAMPLE 34

Eicosylphospho-(N-methyl)-pyrrolidino-ethyl ester $C_{27}H_{56}NO_4P$ MW 489.722

EXAMPLE 35

Eicosenyl-cis-(ω-9)-phosphocholine $C_{25}H_{52}NO_4P$ MW 461.668

EXAMPLE 36

Eicosenyl-cis-(ω-9)-phospho-(N-ethyl-N.N-dimethyl)-ethanolamine $C_{26}H_{54}NO_4P$ MW 475.695

EXAMPLE 37

Eicosenyl-cis-(ω-9)-phospho-(N-cyclopropyl-N.N-dimethyl)-ethanolamine $C_{27}H_{54}NO_4P$ MW 487.706

EXAMPLE 38

Eicosenyl-cis-(ω-9)-phospho-(N.N-dimethyl-N-hydroxyethyl)-ethanolamine $C_{26}H_{54}NO_5P$ MW 491.694

EXAMPLE 39

Effect of various leishmaniasis drugs on the presence of pathogens in the liver of experimental animals (rats) infected with *L. donovani*.

The effect of the phospholipids according to the present invention (hexadecylphosphocholine, octadecylphosphocholine and oleylphospho-(N.N-dimethyl-N-ethyl)-ethanolamine) was compared with the standard therapeutic agent Pentostam used worldwide and the ether lipid $Et_{18}OCH_3$ (1-octadecyl-2-methyl-rac-glycero-3-phosphocholine).

The compounds according to the present invention and $Et_{18}OCH_3$ were administered orally while Pentostam was administered intravenously. It was found that the alkyl phosphocholines with a $C_{18}$ and $C_{16}$ chain were 32-times more effective than the standard therapeutic agent Pentostam while olely-phospho-(N.N-dimethyl-N-ethyl)ethanolamine has a comparable effect to Pentostam.

The results of this experiment are shown in Table 1. The number of pathogens per liver was determined by microscopic analysis.

TABLE 1

Number of leishmania pathogens in the liver after a 3 week period of therapy

| | Pathogens per liver (in millions) | Relative effectiveness (pathogens per liver after Pentostam therapy divided by pathogens/liver after addition of test substance) |
|---|---|---|
| Control | 536.9 | — |
| 1-octadecyl-2-methyl- | 424.7 | 0.007 |

TABLE 1-continued

Number of leishmania pathogens in the liver after a 3 week period of therapy

| | Pathogens per liver (in millions) | Relative effectiveness (pathogens per liver after Pentostam therapy divided by pathogens/liver after addition of test substance) |
|---|---|---|
| rac-glycero-3-phosphocholine[1] | | |
| Oleylphospho-(N.N-dimethyl-N-ethyl)-ethanolamine[1] | 4.7 | 0.7 |
| Pentostam[2] | 3.2 | 1.0 |
| Hexadecylphosphocholine[1] | 0.1 | 32.0 |
| Octadecylphosphocholine[1] | 0.1 | 32.0 |

[1]Alkyl-PC and $Et_{18}OCH_3$ - orally: 5 × 20 mg/kg/week for 3 weeks
[2]Pentostam - iv.: 5 × 120 mg/kg/week for 3 weeks In some additional experiments parasites were no longer microscopically detectable in the liver and in the spleen after single oral dose of 200 mg hexadecylphosphocholine.

EXAMPLE 40

Effect of different leishmaniasis drugs on the presence of pathogens in the spleen The experimental procedure was as described in example 39. The results of these experiments are shown in Table II.

TABLE II

Number of leishmania pathogens in the spleen after a 3 week period of therapy

| | Pathogens per spleen (in millions) | Relative effectiveness (pathogens per spleen after Pentostam therapy divided by pathogens/spleen after addition of test substance) |
|---|---|---|
| Control | 24.3 | — |
| 1-octadecyl-2-methyl rac-glycero-3-phosphocholine | 6.5 | 0.9 |
| Oleylphospho-(N.N-dimethyl-N-ethyl)-ethanolamine[1] | 0.03 | 210.0 |
| Pentostam | 6.3 | 1.0 |
| Hexadecylphosphocholine | 0.01 | 630.0 |
| Octadecyiphosphocholine | 0.01 | 630.0 |

The weak effect of Pentostam in the spleen is surprising. The alkylphosphocholines are in this case >600-fold more effective than the standard therapy.

In several additional experiments parasites were no longer microscopically detectable after a single oral dose of 200 mg hexadecylphosphocholine.

Table III shows the concentration of hexadecylphosphocholine ($C_{16}$—O—PC), octadecylphosphocholine ($C_{18}$—O—PC) and 1-octadecyl-2-methyl-rac-glycero-3-phosphocholine ($Et_{18}OCH_3$) in the organs of the rat after oral administration of 50 μmol/day for 5 days, a pause of 2 days then for a further 4 days at 50 μmol/day.

TABLE III

| Organ | Amount of substance (nmol/g fresh tissue) | | |
|---|---|---|---|
|  | $C_{16}$—O—PC | $C_{18}$—O—PC | $Et_{18}OCH_3$ |
| Serum | 130 | 47 | 5 |
| Liver | 272 | 298 | 36 |
| Spleen | 410 | 424 | 43 |
| Kidney | 853 | 406 | 57 |

It is surprising how well hexadecylphosphocholine and octadecylphosphocholine accumulate in the spleen. It is especially in the spleen that the standard therapeutic agent Pentostam has an extremely low effectiveness. In comparison to this $Et_{18}OCH_3$ is only present in the spleen and in the liver in extremely low concentrations.

EXAMPLE 41

Effect of different leishmaniasis drugs on the presence of pathogens in vitro

Several compounds of the invention were tested against *L. donovani* strain MHOM/IN/54LRC-L.51, isolated from a patient with visceral leishmaniasis. Before use for experiments, the strain was passed through Balb/c mice by intravenous injection.

Promastigotes were cultured in vitro in a mixed medium consisting of one part of HOSMEM and one part of RPMI-1640 (Gibco 041-02400) supplemented with 10% heat-inactivated fetal bovine serum (Gibco 011-06290) at 26° C. Cultures were maintained by seeding $5\times10^6$ promastigotes from 4-day-old cultures into 10 ml fresh medium. The promastigotes were cultured in 24-well-multiplates. After 96 hours of incubation in control or drug-containing media, the number of promastigotes was determined in a Neubauer counting chamber. The 50% inhibitory concentration was calculated graphically. The data is representative of the mean and SD values of 3 different experiments.

TABLE IV

| Compound | $IC_{50}$ Value (µg/ml) |
|---|---|
| hexadecylphosphocholine | 2.07 ± 0.23 |
| octadecylphosphocholine | 0.80 ± 0.20 |
| cis-9-octadecenylphospho-(N,N-diethyl,N-methylamino)ethanol | 2.80 ± 0.50 |
| cis-9-octadecenylphospho-(N,N-diethyl,N-ethylamino)ethanol | 0.66 ± 0.24 |
| octadecylphosphoethanol-(N-methyl)pyrrolidine | 3.59 ± 0.19 |
| octadecylphosphoethanol-(N-methyl)piperidine | 4.90 ± 0.50 |
| trans-9-octadecenylphosphocholine | 0.41 ± 0.14 |

EXAMPLE 42

Effect of different leishmaniasis drugs on the presence of pathogens in vivo

Several compounds of the invention were tested against three strains of Leishmania (*L. donovani* MHOM/IN/54LRC-L.51; *L. donovani* MHOM/IN/80/DDS and *L. infantum* MHOM/ES/86/STI-172). All strains were isolated from patients with visceral leishmaniasis. Before use for experiments, the strains were passed through Balb/c mice by intravenous injection.

Balb/c mice were infected by intravenous injection of a mixture of $10^7$ promastigotes from stationary growth phase and $10^7$ amastigotes which were isolated from the liver or spleen of leishmania-infected mice. Oral treatment with the compounds of the invention was initiated on day 7, at which time the mean parasitic burden was 100 to $200\times10^6$ amastigotes per liver, 1 to $2\times10^6$ per spleen and 3 to 6 amastigotes per microscopic field of 100 hematopoietic cells in bone marrow.

Parasite burden in spleen and liver were determined in GIEMSA's stained impression smears from cut sections by counting the number of amastigotes per 1000 spleen or liver nuclei. The total number of amastigotes per organ was calculated according to Stauber et al. (*J. Protozool.* 5:269–273 (1958)). Parasite suppression (parasite burden of drug treated mice to parasite burden of untreated mice) and parasite killing (parasite burden at the end of treatment to parasite burden at the start of treatment) were calculated according to Baumann et al. (Antimicrob. Agents Chemother. 35:1403–1407 (1991)) for all strains on day 14, for the strain LRC-L.51 in addition on days 21, 25 and 35 post-infectionem. The parasite burden in the bone marrow was examined on days 7 and 35 post-infectionem (strain LRC-L.51).

Table V summarizes the in vivo treatment results of several compounds of the invention in the liver and the spleen of treated mice. The Table shows the parasite burden in the respective organs compared to organs from infected but untreated mice and those treated with the known anti-leishmaniasis agent Pentostam (sodium stibogluconate) (included for comparative purposes only). Compared to the control, the compounds of the invention and the Pentostam significantly reduced the parasite burden in the liver and the spleen. However, it is clear from the Table that the compounds of the invention produced much better results.

TABLE V

| Compound | Dose (mg/kg) | Parasites ($\times 10^6$) | |
|---|---|---|---|
|  |  | Liver | Spleen |
| control | N/A | 520 | 28 |
| Pentostam | 120 (mg/kg) | 3.5 | 6.9 |
| hexadecylphosphocholine | 20 (mg/kg) | 0.07 | 0.008 |
| octadecylphosphocholine | 20 (mg/kg) | 0.07 | 0.015 |
| cis-9-octadecenylphospho-(N,N-diethyl,N-methylamino)ethanol | 20 (mg/kg) | 55 | 3.8 |
| cis-9-octadecenylphospho-(N,N-diethyl,N-ethylamino)ethanol | 20 (mg/kg) | 6 | 0.03 |
| octadecylphosphoethanol-(N-methyl)pyrrolidine | 20 (mg/kg) | 22 | 0.035 |
| octadecylphosphoethanol-(N-methyl)piperidine | 20 (mg/kg) | 65 | 0.35 |
| trans-9-octadecenylphosphocholine | 20 (mg/kg) | 28 | 0.02 |

EXAMPLE 43

In a further experiment, hexadecylphosphocholine was investigated in more detail. The results of a four-week treatment period of Leishmania-infected mice are shown in Table VI. In the liver, Pentostam caused a similar decrease of the parasite load over time compared to hexadecylphosphocholine orally administered at 10 mg/kg. However, an oral dose of 20 mg/kg was significantly more effective, resulting in a 5 to 10-fold higher suppression of parasites (p<0.02). The most striking effect of hexadecylphosphocholine compared to Pentostam is observed in the spleen. In this organ, Pentostam exerts only a moderate suppression of parasite growth compared to control mice. Parasite load slightly increased during therapy, which corresponds to the development of splenomegaly over time. In contrast, oral treatment with 20 mg/kg hexadecylphosphocholine produced a more than three log rank reduction of parasites. Accordingly, spleen weights remained normal as in uninfected mice.

TABLE VI

| Treatment | Spleen Weight (mg) |
|---|---|
| Control | 650 |
| Pentostam (120 mg/kg) | 320 |
| hexadecylphosphocholine (10 mg) | 150 |
| hexadecylphosphocholine (20 mg) | 100 |

What is claimed is:

1. A method of treating Leishmaniasis in a patient having Leishmaniasis, comprising orally or topically administering to the patient an effective amount of at least one compound of the general formula I,

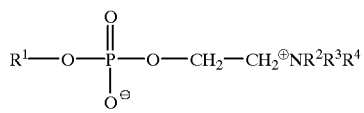

in which $R^1$ is selected from the group consisting of an oleyl, elaidyl, eicosyl, or eicosenyl-cis($\omega$-9) residue and $R^2$, $R^3$ and $R^4$ are independently selected from the group consisting of a methyl, ethyl, hydroxyethyl or $C_3$–$C_6$ cycloalkyl residue.

2. A method of treating trypanosomiasis in a patient having trypanosomiasis, comprising orally or topically administering to the patient an effective amount of at least one compound of the general formula I,

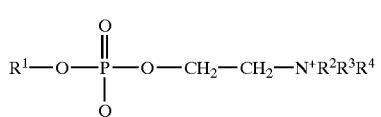

in which $R^1$ is selected from the group consisting of an hexadecyl, octadecyl, oleyl, elaidyl, eicosyl, or eicosenyl-cis($\omega$-9) residue and $R^2$, $R^3$ and $R^4$ are independently selected from the group consisting of a methyl, ethyl, hydroxyethyl, or $C_3$–$C_6$ cycloalkyl residue.

3. The method of any one of claims 1–2, wherein the compound is administered in one or more dosage units each containing the compound in the range of 5 to 2000 mg.

4. The method of any one of claims 1–2, wherein the compound is administered orally.

* * * * *